United States Patent
LePivert et al.

(10) Patent No.: US 8,382,698 B2
(45) Date of Patent: Feb. 26, 2013

(54) SYSTEMS AND METHODS FOR IMPROVING IMAGE-GUIDED TISSUE ABLATION

(75) Inventors: Patrick LePivert, Jupiter, FL (US); Roger Steven Kolasinski, Chantilly, VA (US)

(73) Assignee: Nuvue Therapeutics, Inc., Fairfax, VA (US)

(*) Notice: Subject to any disclaimer, the term of this patent is extended or adjusted under 35 U.S.C. 154(b) by 169 days.

(21) Appl. No.: 12/947,514

(22) Filed: Nov. 16, 2010
(Under 37 CFR 1.47)

(65) Prior Publication Data

US 2011/0112467 A1    May 12, 2011

Related U.S. Application Data

(63) Continuation of application No. 11/097,991, filed on Mar. 31, 2005, now Pat. No. 7,833,187.

(60) Provisional application No. 60/562,759, filed on Apr. 16, 2004.

(51) Int. Cl.
*A61B 17/20* (2006.01)

(52) U.S. Cl. ............................................ 604/22; 606/20

(58) Field of Classification Search .................. 600/437, 600/439; 604/22, 500–522; 606/20, 21
See application file for complete search history.

(56) References Cited

U.S. PATENT DOCUMENTS

| | | | |
|---|---|---|---|
| 4,207,897 A | 6/1980 | Lloyd et al. | |
| 4,900,303 A * | 2/1990 | Lemelson | 604/514 |
| 5,171,217 A | 12/1992 | March et al. | |
| 5,190,766 A | 3/1993 | Ishihara | |
| 5,282,472 A * | 2/1994 | Companion et al. | 600/463 |
| 5,329,927 A | 7/1994 | Gardineer et al. | |
| 5,425,370 A | 6/1995 | Vilkomerson | |
| 5,827,531 A | 10/1998 | Morrison et al. | |
| 5,862,672 A | 1/1999 | Faries, Jr. et al. | |
| 6,039,730 A | 3/2000 | Rabin et al. | |
| 6,235,018 B1 | 5/2001 | LePivert | |
| 6,391,026 B1 * | 5/2002 | Hung et al. | 606/41 |
| 6,461,296 B1 | 10/2002 | Desai | |

(Continued)

FOREIGN PATENT DOCUMENTS

| | | |
|---|---|---|
| CA | 2258619 | 12/1997 |
| FR | 1418132 | 6/1980 |

(Continued)

OTHER PUBLICATIONS

Chao, B. H., Bischof, JC. "Pre-treatment inflammation induced by TNF-alpha augments cryosurgery injury on human prostate cancer", Cryobiology, 49:1:10-27, (2004).

(Continued)

*Primary Examiner* — Nicholas Lucchesi
*Assistant Examiner* — Gerald Landry, II
(74) *Attorney, Agent, or Firm* — McHale & Slavin, P.A.

(57) ABSTRACT

The cryosurgical kit and method of use relates to the combined use of biodegradable, imageable, drug(s) carriers, vectors or microcapsules deposited into a target tissue region inside a body and the controlled cooling of the target tissue region. A minimally invasive method of treatment that applies a cooling device to a selected tissue region, uses a vibrating resonant frequency delivery device to inject drug(s) carriers (microcapsules) containing therapeutic and contrast agents into tissue region(s) submitted to cooling temperatures, successive real-time imaging of the microcapsule deposition and later detection of the progressive degradation of microcapsules with ultrasound imaging which provides estimation of sustained release rates and for planning re-dosing regimens. The thermosensitive microcapsules preferably contain ethiodol, a contrast agent for Ultrasound and/or X-Ray imaging, and cytotoxic drug (s).

10 Claims, 5 Drawing Sheets

U.S. PATENT DOCUMENTS

| | | | |
|---|---|---|---|
| 6,623,430 | B1 | 9/2003 | Slayton et al. |
| 6,706,037 | B2* | 3/2004 | Zvuloni et al. ............ 606/21 |
| 6,786,902 | B1 | 9/2004 | Rabin et al. |
| 6,788,977 | B2 | 9/2004 | Fenn et al. |
| 6,798,977 | B2 | 9/2004 | Maeda |
| 6,803,052 | B2 | 10/2004 | Faisant et al. |
| 6,918,869 | B2* | 7/2005 | Shaw et al. ............ 600/3 |
| 6,931,026 | B1 | 8/2005 | Lee et al. |
| 7,505,807 | B1 | 3/2009 | Kucharczyk et al. |
| 7,833,187 | B2 | 11/2010 | LePivert et al. |
| 2002/0040220 | A1 | 4/2002 | Zvuloni et al. |
| 2002/0055666 | A1* | 5/2002 | Hunter et al. ............ 600/1 |
| 2003/0039613 | A1 | 2/2003 | Unger et al. |
| 2003/0109821 | A1 | 6/2003 | DeVore |
| 2003/0144570 | A1* | 7/2003 | Hunter et al. ............ 600/1 |
| 2004/0059219 | A1 | 3/2004 | Asafusa |
| 2004/0106841 | A1 | 6/2004 | Shaw et al. |
| 2004/0138562 | A1 | 7/2004 | Makower et al. |
| 2005/0227910 | A1 | 10/2005 | Yang et al. |
| 2006/0095330 | A1 | 5/2006 | Nishikawa |
| 2008/0208052 | A1 | 8/2008 | LePivert et al. |
| 2009/0125087 | A1 | 5/2009 | Becker et al. |
| 2009/0301107 | A1 | 12/2009 | Kammer |
| 2009/0326621 | A1 | 12/2009 | El-Galley |
| 2011/0112467 | A1 | 5/2011 | LePivert et al. |

FOREIGN PATENT DOCUMENTS

| | | |
|---|---|---|
| JP | 3297475 | 12/1991 |
| JP | 7213622 | 8/1995 |
| JP | 2000513963 | 10/2000 |
| SU | 532976 | 11/1978 |
| WO | WO9308751 | 5/1993 |
| WO | WO9639960 | 12/1996 |
| WO | WO9749344 | 12/1997 |
| WO | WO9901157 | 1/1999 |
| WO | WO9901158 | 1/1999 |
| WO | WO9906101 | 2/1999 |
| WO | WO9922809 | 5/1999 |
| WO | WO0245609 | 6/2002 |
| WO | WO2005099367 | 10/2005 |
| WO | WO2006095330 | 9/2006 |

OTHER PUBLICATIONS

J. Joosten et al, "In vivo destruction of tumor tissue by cryoablation can induce inhibition of secondary tumor growth: and experimental study", Cryobiology, 41:49-58 (2001).

Clarke, D. M., Baust, J. M., Van Buskirk, R. G., Baust, J. G. "Chemo-Cyro combination Therapy: An Adjunctive Model for the Treatment of Prostate Cancer", Cryobiology, 42:274-285, (2001).

Mir L. M., Rubinski, B., "Treatment of Cancer with Cryochemotherapy", British journal of cancer, 86:1658-1660, (2002).

De Meester SL, Buchman TG, and Cobb JP., "The heat shock paradox: does NF-B determine cell fate?", FASEB J 15:270-274. (2001).

Jaatela. M., "Escaping cell death: survival proteins in cancer", Exp Cell Res., 248:1:30-43, (1999).

Curry HA, Clemens RA, Shah S, Bradbury CM, Botero A, Goswami P, and Gius D. Heat shock inhibits radiation-induced activation of NF-kB via inhibition of I-B. kinase. J Biol Chem (1999) pp. 23061-23067, vol. 274.

Yoo CG, Lee S, Lee CT, Kim YW, Han SK, and Shim YS. Anti-inflammatory effect of heat shock protein induction is related to stabilization of I-B through preventing I-B through preventing I-B. activation in respiratory epithelial cells, J Immunol (2000) pp. 5416-5423, vol. 164.

Feinstein DL, Galea E, Aquino DA, Li GC, Xu H, and Reis DJ. Heat shock protein 70 suppresses astroglial-inducible nitric-oxide synthase expression by decreasing NF-kB activation. J. Biol Chem (1996) pp. 17724-17732, vol. 271.

Scarim AL, Heitmeier MR, and Corbett JA. Heat shock inhibits cytokine-induced nitric oxide synthase expression by rat and human islets. Endocrinology, (1998) pp. 5050-5057, vol. 139.

Ohnishi T, Wang X, Ohnishi K, Matsumoto H, and Takahashi A. p53-dependent induction of WAF1 by heat treatment in human glioblastoma cells. J Biol Chem (1996) pp. 14510-14513, vol. 271.

Nitta M, Okamura H, Aizawa S, and Yamaizumi M. Heat shock induces transient p53 dependent cell cycle arrest at G1/S. Oncogene (1997) pp. 561-568, vol. 15.

Ayad O, Stark JM, Fiedler MM, Menendez IY, Ryan MA, and Wong HR. The heat shock response inhibits RANTES gene expression in cultured human lung epithelium. J Immunol (1998) pp. 2594-2599, vol. 161.

Fujita J. Cold shock response in mammalian cells. J. Mol. Microbiol. Biotechnol. (1999) pp. 243-255, vol. 1.

Gon Y, Hashimoto S, Matsumoto K, Makayama T, Takeshita I, and Horie T. Cooling and rewarming-induced IL-8 expression in human bronchial epithelial cells through p38 MAP kinase-dependent pathway. Biochem Biophys Res Commun (1998) pp. 156-160, vol. 249.

Nishiyama H, Itoh K, Kaneko Y, Yoshida O, and Funita J. A glycine-rich RNA-binding protein mediating cold-inducible suppression of mammalian cell growth. J Cell Biol (1997) pp. 899-908, vol. 137.

Matijasevic Z, Snyder JE, and Ludlum DB. Hypothermia causes a reversible, p53-mediated cell cycle arrest in cultured fibroblasts. Oncol Res (1998) pp. 605-610, vol. 10.

Kaneko Y, Nishiyama H, Nonoguchi K, Higashitsuji H, Kishishita M, and Fujita J. A novel hsp 110-related gene, apg-1, that is abundantly expressed in the testis responds to responds to a low temperature heat shock rather than the traditional elevated temperatures. J Biol Chem (1997) pp. 640-645, vol. 272.

Holland DB, Roberts SG, Wood EJ, and Cunliffe WJ. Cold shock induces the synthesis of stress proteins in human keratinocytes. J Invest Dermatol (1993) pp. 196-199, vol. 101.

Ohnishi T, Wang X, Ohnishi K, and Takashi A. p53 dependent induction of WAF1 by cold shock in human glioblastoma cells. Oncogene (1998) pp. 1507-1511, vol. 16.

Nishiyama H, Danno S, Kaneko Y, Itoh K, Yokoi H, Fukumoto M, Okuno H, Millan JL, Matsuda T, Yoshida O, and Fujita J. Decreased expression of cold-inducible RNA-binding protein (CIRP) in male germ cells at elevated temperature. Am J Pathol (1998) pp. 289-296, vol. 152.

Ars E, Serra E, de la Luna S, Estivill X, and Lazaro C. Cold shock induces the insertion of a crytic exon in the neurofibromatosis type 1 (NF1) mRNA. Nucleic Acids Res (2000) pp. 1307-1312, vol. 28.

Hanai A, Yang WL, Ravikumar TS. Induction of apoptosis in human colon carcinoma cells HT29 by sublethal cryo-injury: mediation by cytochrome c release. Int J. Cancer. Aug. 15, 2001; pp. 526-533, vol. 93(4).

Forest V, Peoc'h M, Ardiet C, Campos L, Guyotat D, Vergnon JM. In vivo cryochemotherapy of a human lung cancer model. Cryobioloby. (2005) pp. 92-101, vol. 51(1).

Grand RJ, Milner AE, Mustoe T, Johnson GD, Owen D, Grant ML, and Gregory CD. A novel protein expressed in mammalian cells undergoing apoptosis. Exp Cell Res (1995) pp. 439-451, vol. 218.

Clarke DM, Baust JM, Van Buskirk RG, Baust JG. Addition of anticancer agents enhances freezing-induced prostate cancer cell death: implications of mitochondrial involvement. Cryobiology. (2004) pp. 45-61, vol. 49(1).

Gyrd-Hansen M, Nylandsted J, Jaattela M. Heat shock protein 70 promotes cancer cell viability by safeguarding lysosomal integrity, Cell Cycle. Dec. 2004; pp. 184-185, vol. 3(12).

Chappel SA, Owens GC, and Mauro VP. A5. leader of Rbm3, a cold stress-induced mRNA, mediates internal initiation of translation with increased efficiency under conditions of mild hypothermia. J Biol Chem (2001) pp. 36917-36922, vol. 276.

Danno S, Itoh K, Matsuda T, and Fujita J. Decreased expression of mouse Rbm3, a cold-shock protein, in Sertoli cells of cryptorchid testis. Am J Pathol (200) pp. 1685-1692, vol. 156.

Danno, S, Nishiyama, H, Higashitsuji, H, Yokoi H, Xue, JH, Itoh K, Matsuda T, and Fujita J. Increased transcript level of RBM3, a member of the glycine-rich RNA-binding protein family, in human cells in response to cold stress. Biochem Biophys, Res Commun (1997) pp. 804-807, vol. 236.

Ohsaka Y, Ohgiya S, Hoshino T, and Ishizaki K. Mitochondrial genome-encoded ATPase subunit 6 8 mRNA increases in human hepatoblastoma cells in response to nonfatal cold stress. Cryobiology (2000), pp. 92-101, vol. 40.

Le Pivert, M.D., P. J., Renard, Ph.D., M., Aller, Ph.D., Titus BS., K., Doulat, Ph.D., J., Renard, Ph.D., M., and Morrison, Ph.D., D. R.

Ultrasound Guided, Combined Cryoblation and Microencapsulated 5-Fluorouracil, Inhibits Growth of Human Prostrate Tumors in Xenogenic Mous Model Assessed by Luminescence Imaging, Technology in Cancer Research & Treatment, (2004) pp. 135-142, vol. 3(2).

Sonna, LA, Kuhlmeier, MM, Carter HC, Hasday, JD, Lilly CM, and Fairchild, KD. Effect of moderate hypothermia on gene expression by THP-1 cells: a DNA microarray study. Physiol. Genomics 92006), pp. 91-98, vol. 26(1).

Wang H, Wang H, Zhang W, Huang HJ, Liao WS, Fuller GN. Analysis of the activation status of Akt, NFkappaB, and Stat3 in human diffuse gliomas. Lab Invest. (2004) pp. 941-951, vol. 84(8).

Katz, A and Rewcastle J. The current and Potential Role of Cryoablation as a Primary Therapy for Localized Prostate Cancer, Current Oncology Reports (2003) pp. 231-238, vol. 5.

Onik G. Image-Guided Prostate Cryosurgery: State of the Art, Cancer control (2001) pp. 522-531, vol. 8(6).

Tian-Hua Yu, Jingliu, Yi-Xin Zhou. Selective freezing of target biological tissues after injection of solutions with specific thermal properties. Cryobiology, (2005) pp. 50, 2, 174-182.

Han, B, Ifftekhar, A., Bischoff, J. Improved cryosurgery by use of thermophysical and anti-inflammatory adjuvants. TCRT, (2004) pp. 3, 103-111.

Kaneko, Y, et al. A novel hsp110-related gene, apg-1, that is abundantly expressed in the testis responds to a low temperature heat shock rather than the traditional elevated temperatures. J Biol Chem (1997) pp. 2640-2645, vol. 272.

De La Taille, et al. Cryoablation for clinically localized prostate cancer using an argon-based system: complication rates and biochmical recurrence. BJU (2000) pp. 281-286, vol. 85(3).

Le Pivert, M.D., P. J., Morrison, Ph.D., D. R., Haddad, Ph.D. R. S., Doulat, Ph.D., J., Renard, Ph.D., M., Aller, Ph.D., A., and Titus BS., K., Percutaneous Tumor Ablation: Microencapsulated echo-quided Interstitial Chemotherapy Combined with Cryosurgery Increases Necrosis in Prostate cancer (2008).

\* cited by examiner

|  |  | N | TUMOR RADIUS (mm) | NECROSIS RADIUS (mm) | DAY 3 IB KILL RATIO |
|---|---|---|---|---|---|
| COMBINATION (CA+MCC/5-FU) | Mean S.D. | 11 | 6 1 | 3.8 0.3 | 0.54 0.12 |
| CRYO (CA) | Mean S.D. | 12 | 4.7 0.9 | 3.1 0.6 | 0.40 0.9 |

FIG. 4A

| Treatment (A549.Dec.2004) | Nb Tumors Treated | Nb Tumors Cured | Day of Cure | Percent cure at 3 weeks |
|---|---|---|---|---|
| Combined Therapy (cryo+5FU) | 16 | 4 | 11 to14 | 25% |
| ucaps Chemo (5FU) | 16 | 0 |  | 0% |

FIG. 4B

SYSTEMS AND METHODS FOR IMPROVING IMAGE-GUIDED TISSUE ABLATION

RELATED APPLICATIONS

This application is a continuation of U.S. patent application Ser. No. 11/097,991, filed on Mar. 31, 2005 now U.S. Pat. No. 7,833,187, which claims priority of U.S. Provisional Patent Application No. 60/562,759, filed on Apr. 16, 2004, the contents of each are incorporated herein by reference.

FIELD OF THE INVENTION

This invention relates to the field of cryosurgery and the treatment of tumors.

BACKGROUND OF THE INVENTION

Modern approaches to minimally invasive ablative treatment of solid tumors involve the use of miniature instruments, and combined treatments like thermal ablation and systemic chemotherapy.

Cryosurgery is now recognized as an efficient, thermo-ablative, minimally invasive, method for a large number of solid tumors like prostate, lung, liver, kidney, to cite only a few. Cryosurgery affects tumor tissue viability in three different ways with immediate and delayed alterations: the freezing of tumor cells, and vasculature results in tumor kill through direct cell alterations, and indirect vascular occlusion.

Recently another mechanism of cell kill consecutive to cryothermal changes is apoptosis, a programmed, gene-regulated, cell death that has been shown predominant at the margins of a cryolesion, both at freezing and sub-freezing temperatures. The changes in microvasculature are now thought to be the main factors of tissue necrosis induced by freezing methods.

To achieve cryoablation, the entire tumor must be frozen to "kill" temperatures in the range of −40° C., the Freeze/Thaw, F/T, cycle must be repeated, and the kill temperature, out to the tumor margins, must be maintained for a few minutes, designated the, "hold time," during cryosurgery. Despite a strict adherence to these standards, which are time consuming, certain tumors like prostate or metastatic liver cancer show a 20 to 40% post procedure recurrence. Whether the cause of this failure is disease-based or technique-related, it's recognized that cryosurgery needs the support of adjunctive therapy in the form of chemo- or radiotherapy to increase the rate of cell death at margins of the cryogenic lesion where the cell fate is known to be in balance for several days post treatment.

The pretreatment of a tumor with a pro-inflammatory protein like TNF-, based on the hypothesis that vascular-mediated injury is responsible for defining the edge of the cryolesion in microvascular-perfused tissue, augments the cryoinjury that occurs at much higher temperatures, close to 0° C., due to a inflammatory pre-sensitization of the microvasculature, Bo H. Chao, Xiaoming He and J. C. Bischof, Cryobiology 2004, 49, 10-27. Although this pretreatment seems better in terms of ablation completeness, it doesn't act directly on tumor cells and particularly on cells that may have escaped the margin of the cryolesion.

Hence there is a clear need for agents, neo-adjuvant or adjuvant to cryosurgery that could increase the cryosurgical kill as well as the tumor cell kill within and outside the frozen zone, while sparing the normal cells and tissue structures.

Systemic chemotherapy has long been used to enhance the kill effect of cryosurgery on experimental and human solid tumors, but results have been inconsistent. Probably because the combined treatments weren't based on sound protocols defining the drug, dosages, route of administration and timing of applications to cite only a few preeminent parameters. Since most common chemotherapeutic drugs initiate apoptosis in cancer cells, and given that a similar effect is observed with sub-freezing temperatures, the timely conjunction of each method has been sought for optimizing tumor cell death at tumor margin. A number of papers have shown that in vitro moderate freezing temperatures combined with low dose chemotherapy increased the rate of cell death for prostate and colo-rectal cancer cells. However, these findings weren't transferred to in vivo experiments. The issue with systemic chemotherapy is that the side effects cannot be prevented, tumor exposure to therapeutic doses is intermittent, and tumor penetration is unpredictable. Another drawback is that tumor cells still need to be frozen. Therefore, there is a risk of damage to neighboring normal tissue by excessive freezing. Moreover, the cytotoxic drug penetration into tumor may be difficult and imprecise upon initiation of cryo-induced microvascular impairments particularly if a precise timing between the drug administration and the cryo-application hasn't been respected. The drug properties are also critical and should be selected on the basis of their ability to act on the tumor cells as well as on the microvascular network constituents. There is a need for a more effective cryochemotherapy combination that would increase the tumor cell kill both in the frozen and unfrozen regions of the cryo-application and expose the cells and/or the microvascular bed to effective concentrations of drug for longer durations, while preventing systemic adverse effects.

Intra-tumor chemotherapy using different drugs and vectors or carriers of those drugs has been proposed to improve local delivery of chemotherapeutic agents and decrease their side effects. These new formulations, microspheres, liposomes, matrixes, etc., have the capability of slowly releasing the active component at therapeutic dose by diffusion through membrane and/or progressive degradation/lysis at body temperature. Such sustained release exposes cells to higher concentration of the cytotoxic drug for longer periods of time, prevent side effects and result in better outcome. The agents' carriers are deposited locally or into the vascular bed of the tumor as the sole treatment and/or as a pre-adjuvant or adjuvant therapy to surgical excision, radiation therapy, 5-FU encapsulation and glioblastomas, as taught in U.S. Pat. No. 6,803,052, or microwave hyperthermia, as taught in U.S. Pat. Nos. 6,788,977 and U.S. Pat. No. 6,623,430. For the latter, moderate hyperthermia of the target organ, is triggering the release of the drug out of the thermo-sensitive, solid-matrix microsphere containing doxorubicine, Thermodox®. The company has initiated clinical studies for a combined treatment of liver malignant tumors that inject Thermodox® at periphery of a radiofrequency lesion, where tissue temperature is about +41° C. These treatments rely for their safety and efficacy on the precise, homogeneous deposition and known degradation rates of the carriers. Since these carriers cannot be imaged, there is no method to determine, in real time, the optimum delivery, in terms of spatial distribution and dose. Such assessments are based only on direct visualization, at open surgery, and on indirect measurement of tissue temperature.

Cryosurgery has been associated with curettage and topical chemotherapy with 5-FU for the treatment of actinic keratosis (AK) a pre-cancerous lesion that usually doesn't metastasize. One of the topical ointments Carac Cream contains 0.5% fluorouracil, with 0.35% incorporated into a patented porous microspheres, Microsponge®, composed of methyl methacrylate. However, the prescribed mode of application doesn't call for a specific geometric deposition of the cream, i.e. preferentially at lesion margins, or timing between cryoablation and chemoablation, and therefore isn't optimized to increase the cryo-kill at warmer temperatures and spare the neighboring normal skin.

Various drug mixtures and carriers containing cytotoxic agents have also been injected directly into the vascular bed of tumor through selective or supra-selective catheterization with adapted instruments. The combination of cytotoxic drug with agents of embolization is used to increase the cell death rate by submitting the tumor cells to elevated drug concentrations and ischemia consecutive to microvascular thrombosis. However, embolization techniques aren't easy, require specific and costly technologies and highly specialized departments, and the drug distribution isn't necessarily homogeneous.

A major drawback of the sustained-release drug carriers—delivery carriers (microspheres, liposomes, microcapsules, gel-foam particles, etc.) is that they aren't visible continuously, in real time using most of the available clinical imaging systems, i.e. ultrasound imaging, C-T radiography or fluoroscopy. As a consequence, the physician doesn't know whether the desired target site of deposition has been reached, nor whether the drug carriers are correctly distributed throughout the tumor or target tissues. To compensate for this drawback the mixtures or emulsions of insoluble contrast agents, like Ethiodol® carriers have been mixed with the drug solutions or carriers just prior to administration. However since the carrier and the contrast agent diffusion/distributions in tissues are different, the imaging of the contrast in the mixture doesn't give precise clue of the carrier location beyond a few minutes period. Another drawback is that a pinpoint placement of the depots into tumor requires a Perfect visibility of the delivery device throughout the procedure until the delivery tip reaches the targeted tumor region, particularly for deep-seated lesions.

Although a number of techniques are described to increase the echogenicity of delivery needles or catheters during various procedures, their characteristics aren't helpful for visualization in deep-seated lesions, where their effectiveness would be most desirable.

Another aspect of the drug release from biodegradable carriers can be effected in multiple ways: either spontaneous at core body temperature, or at-will triggered. Controlled release aims at: increasing effectiveness of drug by immediate and/or sustained release of large volume of drug, preventing complications, such as embolization, from carriers that have unwillingly moved to unwanted location, allowing for combined technologies that sensitize tumor cells by increasing their permeability to the drug.

Finally, since the cellular heterogeneity of malignant tumors is one of the major factors that explain tumor resistance to an initially effective single drug chemotherapy it would be an advantage to encapsulate a mixture of drugs that would overcome this chemo-resistance. Currently available sustained release systems encapsulate only a single drug.

There is a need for:
1. A minimally invasive, combined cryoablation method that would simultaneously expose the periphery of a tumor to effective concentrations of agent(s) for longer durations, while preventing systemic adverse effects, and sparing the patient's immune system.
2. Agent (s) or microcapsules of drugs, neo-adjuvant or adjuvant to minimal access computer-aided and image-guided cryosurgery, that would increase the safety and efficacy of the cryosurgical kill as well as the tumor cell kill while sparing the normal cells and tissue structures.
3. A new formulation of agent(s) or microcapsules or a combination of them that would allow for controlled and/or sustained release at targeted location(s) into tumor. Such formulation would simultaneously co-encapsulate contrast agent(s) and a cellular and/or vascular cytotoxic drug or drug(s) so that ultrasonic (US) imaging will monitor continuously the delivery device, the deposition and degradation of the agents' carriers particularly for deep-seated lesions.
4. A method that would optimize the selective tumor kill of the combination of the cryothermal ablation, of the imageable biodegradable drug(s) carriers, and of the imageable delivery device.
5. A Ultrasound-guided and minimal access combined procedure in which the drug-delivery and the drug-vector systems can be continuously imaged in real time so that the drug deposition site(s) as well as the drug release from the drug-vector degradation can be monitored over time at site of deposition.

SUMMARY OF THE INVENTION

It is an object of the invention to teach novel materials and procedures for enhanced safety and efficacy of focal cryoablation of unwanted tumor tissue while preserving the body's immune system.

It is a further object of the invention to teach a method that decreases the operative time for cryoablation of a tumor target, and protects surrounding tissues from harmful cooling.

It is a further object of this invention to teach a method that optimizes the combined delivery of cryothermal energy and of the therapeutic agents', and carriers thereof, to the target tumor tissue.

It is an even further object of the invention to teach a method that uses repeated challenges or treatments of the target tissue or tumor with the imageable agent(s) or microcapsule carriers of those agents to facilitate and complete the initial combined treatment.

It is yet another object of the invention to teach using, during cryoablation of a tumor, a vibrating delivery device that allows for continuous, real time visualization through Ultrasound imaging assuring the precise delivery of any needles, probes, and catheters used for the precise intratumor deposition of unique thermosensitive, biodegradable, and imageable carriers, such as microcapsules, containing imaging contrast agent(s) and combinations of tumor inhibiting drugs. A synergistic kill effect on tumor cell results from the degradation of the thermosensitive carriers during transient controlled freezing/cooling of the target margins and after the tumor has returned to its pre-cooled normal temperature.

BRIEF DESCRIPTION OF THE DRAWINGS

FIG. 4A is a table illustrating the effect of cryoablation and/or microencapsulated 5-fluorouracil on prostate tumor necrosis. The kill ratio of the ice ball is the ratio of tumor necrosis measured three days postoperatively to ice ball surface. It reflects the overall destructive effect of the frozen part of the thermal lesion. Combined therapy gives a larger mean necrosis radius than cryoablation alone. This difference is significant: P<0.004.

FIG. 4B is a table illustrating the cure rate observed with a cytochemotherapy protocol that injected interstitially volume-adjusted doses of μcaps 5-FU at the time of cryoablation perioperatively, and during the post-operative period at day 7 and day 14. Cryoablation was purposely sparing the peripheral part of bioluminescent lung tumor (A549 luc) where the pcaps depots were injected.

DETAILED DESCRIPTION

Figure 1:
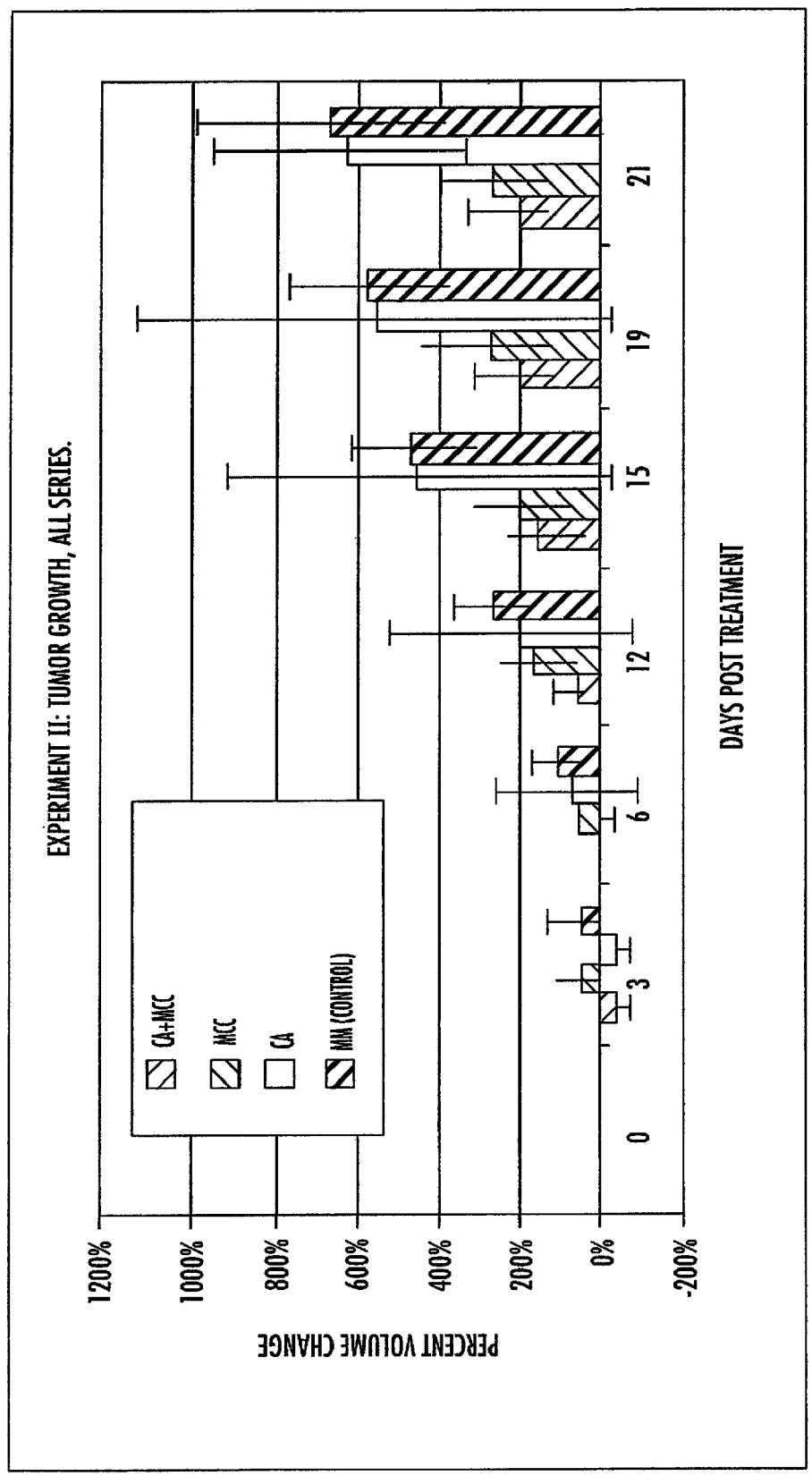
FIG. 1 illustrates enhanced inhibition of viable tumor cell growth in human prostate tumors receiving combined treatments (Cryo+5FU mcaps) compared to increased tumor cell growth of the tumors treated with only cryosurgery. This figure shows the synergistic effect of the combination of cryosurgical ablation and microencapsulated chemotherapy deposited at frozen region margins.

This invention incorporates and improves on the subject matter of several patents: e.g., U.S. Pat. No. 6,235,018 for monitoring cryosurgery; U.S. Pat. No. 5,425,370 that oscillates the delivery device(s) at its resonant frequency; and U.S. Pat. No. 5,827,531 that discloses the unique microcapsules. All of these patents are incorporated herein by reference. The patent material is summarized below for a clear understanding of the objects and advantages of the present invention.

The computer-aided monitoring method disclosed in U.S. Pat. No. 6,235,018 predicts, in real-time, the extent of the ice ball kill zone, and, alone, or in conjunction with conventional imaging techniques, such as, Ultrasound, "US", Computerized Tomography, "CT", Magnetic Resonance, "MR" allows a precise location of the target regions for complementary treatment with unique imageable drug(s) carriers.

The imageable drug(s) carriers of this invention are unique microcapsules. The new microcapsules are based on (1) microcapsules originally found in U.S. Pat. No. 5,827,531, now modified to make them echogenic using one or more dense contrast imaging agents adapted to various imaging modalities co-encapsulated with the drug(s) solution; (2) 98% payload volume of the microballoon type of microcapsules is drug/contrast; (3) multiple drugs in single microcapsules; and (4) microcapsules with selected thermosensitivity of the outer membrane which allows slow lysis of the microcapsules after they are deposited in the body and thereby sustained, bulk, release of the therapeutic agents contained therein.

The precise deposition of the imageable drug(s) carriers is made possible in superficial as well as in deep-seated tissues with a vibrating delivery device(s) of U.S. Pat. Nos. 5,425, 370 and 5,329,927. This device allows for the pinpoint delivery and continuous, accurate visualization of minimally invasive, indwelling diagnostic needles and therapeutic probes and catheters in real-time, via the use of resonant frequency Ultrasound, which allows for the positioning, interstitially, of these devices into targeted tissue regions via direct, minimally invasive, endoluminal, and/or endovascular (intra-arterial or intravenous) approaches. The spatial deposition of carriers is into and preferably at tumor margins. The latter must coincide with thermal margins of ice ball; the deposition is followed by a controlled release of drug(s), from through-wall diffusion and/or vector degradation, with adapted needle(s), catheter(s), and/or probe(s). Ultrasound imaging allows for real-time visualization and most effective loading of tumor tissue with the carriers as well as their degradation, which corresponds to the disappearance of their ultrasonic image.

The relative timing of cryoablation and deposition of imageable carriers insures a synergistic effect of the combined treatment and optimal target ablation. The initial deposition of drug carriers is made just before or after the cryogenic thermal insult. Subsequent injections are based on release rate and cytotoxicity studies in vitro as well as on tumor response in vivo and on repeated US imaging of the tumor and implanted carriers. Hence, ultrasonography, a simple and readily available technology, allows monitoring the completion and effectiveness of treatment, and the occasional need for re-dosing. We have demonstrated on preclinical tests that such combination therapy, comprised of partial freezing of tumor before drug carriers injection, has an inhibitory effect on tumor growth that is superior to each modality used individually on hormone-refractory prostate cancer and on non small-cell lung cancer.

The present invention extends the safety and efficacy of tumor cryoablation. Currently the peripheral margin of an ice ball has to overlap the margin of a tumor by a few $10^{th}$ of mm to insure complete destruction of the tumor. With the use of the vibrating Ultrasound cryoprobes and delivery devices there is assurance of the injection and precise delivery of encapsulated agents at the margin of the ice ball, we extend the kill zone, i.e. cryonecrosis, toward the ice front over a few mm. The consequences are that the necrosis front comes closer to the visible ice front and to its image under US, CT or MR imaging, and that surviving tumor cells located at ice ball and tumor margin are now lethally injured. Since such necrosis now occurs at warmer temperature, there is less risk of damaging normal tissue in the vicinity of the ice ball. It is also much easier to predict the extent of the tissue kill with imaging techniques like ultrasound since the hyperechogenic ice front will closely correspond to the subsequent necrotic zone. Given that we are using in conjunction with US imaging an impedance-based monitoring method, described in U.S. Pat. No. 6,235,018, we can easily confirm the location of the kill zone of the ice ball.

This invention gives much better outcomes than systemic chemotherapy since the deposition of the drug at optimal concentration, and at the right location is insured with the delivery device and the imageable microcapsules of carriers of the therapeutic drug (s) carriers.

The advantages of the procedure will appear at description of the following example. For instance, during prostate cancer ablation, i.e. cryoprostatectomy, the posterior part of the gland must be separated from the anterior rectal wall with saline solution or other protective material so that the ice balls created by multiple probes encompass the prostate capsula but do not harm the fragile rectal tissue structure and vessels. This invention will allow injecting the peripheral part of the gland and the capsula with encapsulated drug and limited freezing of the gland and its capsula without over-freezing. A treatment modality that directly delivers the cytotoxic drug(s) to the cancerous cells surviving or escaping the cryoapplication, and a new formulation that delivers continuous drug(s) concentrations able to kill hormone-refractory cancer cells.

Our combined procedure decreases the operative time since we have demonstrated that a single freeze and thaw application without "hold-time", and warmer tissue temperatures are sufficient to entail the enhanced kill. Thereby improving the patient ability to recover more quickly with reduced complications rates, side effects, such as impotence, or recurrences. The timing of the drug carriers delivery relative to the cryothermal treatment is critical in determining the resulting microvascular antitumor effect. Since the microvascular changes following cryosurgery are completed within the first 2 hours following application the best window for eliciting a synergistic effect is just before or after the cryoapplication. Our preclinical studies on a prostate and lung cancer have shown a significant tumor inhibition when microencapsulated 5-FU deposits were injected at tumor margins during tumor defrost or immediately after.

The imaging encapsulated contrast agent(s) gives unique capabilities to our treatment method. We can monitor microcapsules with CT, or now Ultrasound (US), to determine and control most effective loading of tumor tissue and when the microcapsules degrade. When they are no longer visible, we know that there are few, if any, left so that another dose can be applied in another region. The uniqueness of the imageable microcapsules and vibrating delivery device allow us to distribute them homogeneously into tumor. By knowing continuously the location of the delivery device shaft/tip we can safely and precisely inject the drug carriers to the targeted zone of tumor or tissue, everywhere in the body, including the cardiac cavity and muscle. The uniqueness of our treatment combination lays in the fact that microcapsules with adjusted thermosensitivity are used simultaneously and sequentially to optimize the tumor kill. Highly thermo-labile microcapsules are preferably deposited at the margin of tumor tissue submitted to hypothermia and partial freeze for fast drug release (over a few hours), and lesser thermosensitive microcapsules are used for sustained drug release on the remnant tumor over a longer period of time (12 to 15 days). Therefore, ultrasound imaging performed during the perioperative period, immediately preceding and/or following the procedure shows the accuracy of microcapsule placement, efficacy, and the completion of the thermal treatment based on the disappearance of the faster lysing (more thermosenstitive) type of microcapsules.

Since intra-tumor delivery of the drug at the right location for controlled period of time is made possible with extreme precision, the goal, is to deliver adequate, i.e. therapeutic drug concentration. To enable custom design of treatment regimens for different human tumors, we use in vitro cytotoxic assays to determine effective drug release and tumor cell inhibition, then we use in vivo bioluminescent tumor model to estimate near-term effectiveness of the combined therapies and develop scientific basis for re-dose regimen Our method is quite different from those that use systemic or local drugs to sensitize tumors to cryosurgery or other chemical, thermal or radiation treatments. We are focused on the optimization of the synergistic effects of tissue freezing/hypothermia and encapsulated chemotherapy/agent(s) at tumor margins. We are seeking to perform a deposition of the imageable encapsulated drug(s) preferably in peripheral tumor zones where interstitial pressure is lower, where microvascular density is higher, where migrating tumor cells may have already escaped the tumor bulk (micrometastases) and where tumor is submitted to freezing and hypothermia. Moderate tissue hypothermia is known to elicit vasomotor reflexes, stasis, and increased permeability in the microvasculature, resulting in tissue ischemia and apoptosis. Some cytotoxic drug, like 5-fluorouracil, are known to elicit microvascular changes which effect endothelial cells, angiogenesis (anti-angiogenic effect), and enhance hemostasis as well as tumor cell apoptosis.

The peripheral margins of the tumor along with a margin of adjacent normal tissue, i.e. the safety margin, are the sites where we are precisely injecting our drug (s) carriers. Such procedure releases the active drug closer to the developing microvasculature in zones of low interstitial pressure where the drug can easily be transported to the most metabolically active target cells.

We have calculated that the radius of the hypothermic zone, i.e. from 0° C. to +25° C., from the cryoprobe center is about twice that of the frozen zone during experiments on xenogenic prostate and lung tumor models. Since we have observed an increased cell kill when microcapsules 5-FU were deposited in tumor regions submitted to temperatures ranging from +5° C. to +12° C., and given that microcapsules are deposited at tumor margins, we can easily decide the location of the ice front border, always at 0° C., by reference to the tumor margins. Ultrasound imaging show real-time images of the advancing ice front edge, an hyperechogenic rim, when it comes close to the tumor margins. However, since the entire ice-ball cannot be imaged by ultrasonography (shadowing behind the ice front), we use in conjunction the help of our impedance-based monitoring method to predict the location of the destructive ice front. The present invention described above uses a US-guided minimally invasive tumor tissue ablation with a cryosurgical probe(s), an imageable vibrating delivery device and imageable drug (s) carriers. The cryosurgical probe induces and the monitoring system depicts the formation of a lethal frozen zone in the target tumor surrounded by a sub-lethal zone. US imaging of the ice front edge allows for assessing its extension to the tumor margins. Deposits of small volumes of thermosensitive microcapsules containing the cytotoxic drug(s) along with the imageable contrast agent are injected percutaneously and distributed into tumor periphery with adapted imageable delivery device. In a preferred embodiment, the major steps in this process are: 1) Fabrication of the special imageable cytotoxic microcapsules (μcaps); 2) Ultrasound imaging to characterize the location, size, and shape of the target tumor, 3) Ultrasound guidance and precise positioning of the vibrating cryoprobe(s) tip at selected location into tumor according to the operative planning 4) computer-aided and image-guided cryoablation, with a single freeze session per probe (if multiple probes have been inserted) and no hold time at minimal temperature, to monitor ice ball growth within the edges of the tumor, and simultaneous creation of a hypothermic region in the perimeter of the tumor [and the adjacent tissues]; 5) Percutaneous injection of the microcaps in the hypothermic regions of the tumor and surrounding tissue, using ultrasound visualization to insure precise delivery and distribution of the cytotoxic microcapsules, peripheral to the lethal zone of the ice ball; and 6) sequential ultrasound imaging of the microcapsules deposits so that their degradation rate can be monitored and the time for re-dosing be determined with accuracy.

Specifications of a Preferred Embodiment

Fabrication of multilamellar microcapsules—Microcapsules are made by a low shear, forced fluid flow of two of more liquids, and interfacial coacervation, followed by harvesting and washing in 0.9% saline to produce microcapsules containing 80% by volume of an aqueous solution of 2% w/v 5-Fluorouracil and 20% v/v of a dense, echogenic contrast [Ethiodol®, a iodinated poppy seed oil] surrounded by a thin multiple polymer membrane which occupies less than 3% of the total volume of said microcapsule.

A characteristic of these liquid-filled, microballoon type of microcapsules is that the thin outer membrane is more stable when stored in suspension at temperatures between 4-26° C. However, the outer membrane of these microcapsules will slowly dissolve at body temperature (37+/−2° C.) such that at least 10% of the microcapsules will rupture and release their contents within the first 48 hours after being deposited into a target tissue. Typically, the lysis of these microcapsules will continue over a 10 to 14 day period, thereby providing sustained release of the drug contents to achieve improved therapeutic effects compared to injections or deposits of the free drug solution.

Another preferred embodiment includes similar microcapsules, which contain a plurality of drugs within the encapsulated liquid phases. Herein, different drugs with solubility in either the aqueous phase or the organic solvent phase or contrast agent phase (oil) can be encapsulated and delivered in the same microcapsules. The combination of drugs contained in these microcapsules is designed to be complimentary, such that the local therapeutic effects on cells and tissues will be greater due to the additive or potentiative effects of the combination compared to the effects of the individual drugs alone. The release of the multiple drugs can be achieved by diffusion through the microcapsule outer membrane or by lysis of that membrane and bulk release of the total contents (drugs) contained within the microcapsule. An alternate embodiment would be the use of a suspension containing a mixture of different microcapsules, containing individual drugs, whereby the simultaneous delivery of the mixed suspensions of those different microcapsules (drugs) can provide the same complimentary and sustained release of the encapsulated drugs to achieve improved therapeutic effects compared to deposition of the individual free drugs by separate delivery methods.

The average microcapsule diameter is 8-16 microns, with a size distribution wherein 80% of said microcapsules fall into a range between 1-30 um. The drug loading of 5-FU is typically 0.36 ng/μl of microcapsule suspension [65,200 μcaps/μl].

Ultrasound imaging—Imaging of the target tumor is accomplished using a commercial, medical, ultrasound system with a handheld transducer operating at 12 MHz. US visualization of the cryoprobe tip placement within the tumor, ice ball growth, and local deposition of microcapsules is made in real time using the U.S. display. Tests on human prostate and lung subcutaneous tumors, grown in xenogenic mice used a portable black and white ultrasound device (Hawk 2102 & Merlin 1101, BK Medical Systems, FL USA, with a, Model 8570 12 MHz linear array transducer).

Cryoablation and hypothermia treatment: (see FIG. 1) Under general anesthesia a 3 mm diameter cryoprobe (Critical Care Innovations, Inc., VA, USA) is inserted vertically into tumor through a skin puncture. A 0.5 mm bead wire insulated (PFA Teflon®) type T thermocouple (Omega, Conn., USA) is placed percutaneously into tumor a few mm off the probe wall. The probe tip end contains a thermocouple located at 5 mm from tip end. Both thermocouples are connected to a data-logging module (Super Logics, CP 8218) and to a laptop (HP Pavilion ze 4145) running a proprietary thermal monitoring and simulation software. During the cryosurgical procedure this software measures probe temperatures and uses them to predict: 1) the tumor temperature (+/−2° C.), (assuming cylindrical symmetry, by solving the equation of thermal diffusivity), and 2) ice ball formation and temperatures of tumor and adjacent tissues at various distances beyond the ice ball. Cryoablation of experimental prostate (DU145) and lung (A549) tumors consisted in freezing a portion of the tumor from skin surface to the deep margin and leaving a volume of peripheral tumor unfrozen but being submitted to hypothermia. The probe tip was purposely not centered in tumor so that the ice ball never overlapped the entire tumor area. Hence, the frozen zone of the tumor was clearly distinguishable from the hypothermic zone. A single freeze/thaw (F/T) cycle was used without hold time. Within 5 minutes the ice ball thawed spontaneously at room temperature. The duration of hypothermia zone in ice ball region was estimated to be from 15 to 30 min. A time that is clearly within the accepted duration of exposure to freezing temperatures for tumors during conventional cryoablation. The puncture was sealed with cyanoacrylate adhesive.

Intratumor percutaneous deposition of imageable cytotoxic microcapsules: At the end of the freezing cycle, a 25 gauge short-beveled needle is inserted, using the U.S. visualization to locate the needle tip and echogenic deposits of 5-FU μcaps that are just peripheral to the ice ball margin. This is a unique technique that can confirm in real-time the proper distribution within the tumor and estimate if there are any volume of tumor that require complementary injections immediately or later. Each injection contained, based on the total tumor volume, from 20 up to 200 ml of PBS suspension deposited in multiple peripheral sites of the tumor using a parallel-row technique or field block technique.

Each microcapsule injection contained 1.3×10 6 microcapsules/20 ml comprising a local dose of 7.2 ng of 5-FU per injection with a calculated total dose of 25.8 ng of 5-FU/μm of tumor. In the days following the combined treatment, US imaging of the target tumor allow assessment of tumor margins, tumor necrosis consecutive to treatment and tumor shrinkage, as well as microcaps depots visualization. The disappearance of the echogenic depots from image is related to a residual volume of less than 1.8 μl of pure microcapsules left in any given location. Percutaneous intra-tumor re-injections of volume-adjusted dose of μcaps is performed based on clinical parameters (tumor volume, necrosis), optical imaging (decrease in luminescence intensity) and on the; leaps degradation rate as evidenced by US imaging.

Figure 2:
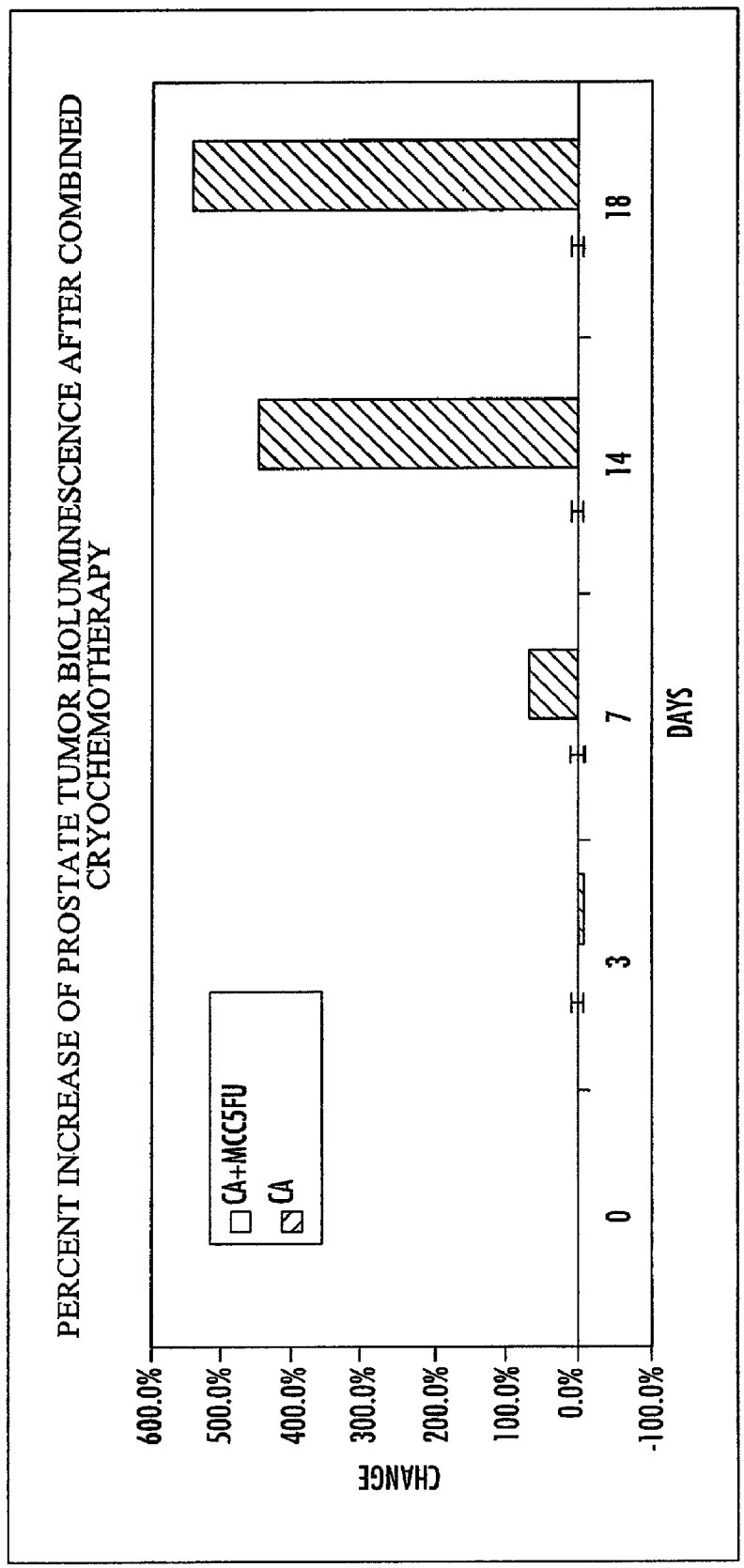
FIG. 2 illustrates the sustained release of microencapsulated drug. Comparison of viable tumor cell growth (bioluminescence recorded from Luc+human prostate tumor cells) showing the reduction in viable cells resulting from cryoablation alone (CA), and the prolonged effect three weeks of the combined cryo-chemotherapy treatment (CA+MCC). This figure illustrates the long lasting action of the sustained release of the microencapsulated drug.

The results of this combined modality show that this new modality of cryo-chemotherapy is far more effective in inhibiting tumor growth than either individual treatment (FIGS. 1 and 2). The inhibitory effect appears at sub-toxic doses of 5-FU, as described above. Moreover, this effectiveness doesn't require that the cell be submitted either to low negative temperature, i.e. under −20° C., to intracellular freezing, to complete or partial extra cellular freezing or to repeated F/T cycles. We have calculated that the temperature of tumor at the sites of microcapsules deposition was about 12° C.+−4° C.

Since a deep freezing and repeated F/T cycles aren't required to elicit the inhibitory effect on tumor growth it is another advantage of the procedure to significantly shorten the operative time.

Another advantage of the invention is that the addition of microcaps 5-FU increases significantly the cryonecrotic area (see FIG. 4A), which in our experiments comes closer to the ice ball margin (b/t 0.5 to 1.5 mm). Therefore, with this combined technique, US imaging becomes a valuable tool to predict in real time the future location of the kill margins.

Another aspect of the combination is that it spares the target vicinity, particularly the fragile or risky structures of normal tissues, from being harmed by excessive freezing or long lasting cooling. Moreover, moderate cooling may help these same potentially sensitive structures to resist the action of local chemotherapy, allowing for larger doses to be acting more effectively into tumor. Therefore, the combined therapy increases the safety and efficacy of cryosurgery.

Figure 5:
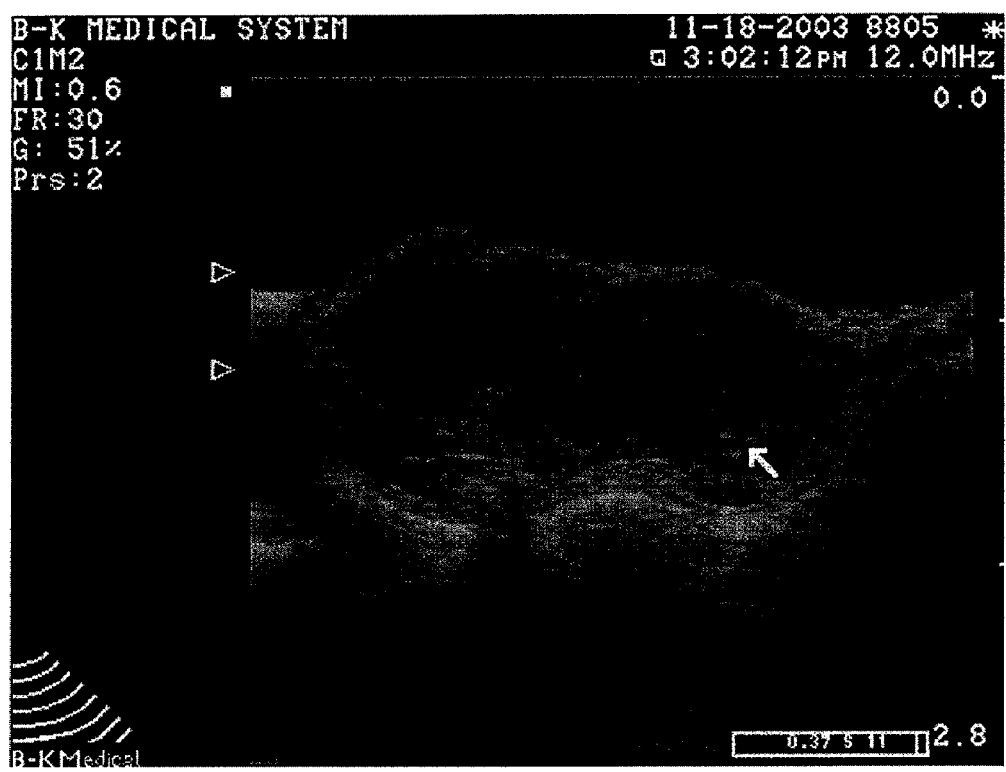
FIG. 5 is an ultra sound image detecting microcapsules captured at real time, allowing deposition of the microcapsules at a precise and targeted location.

Another advantage of our invention is that the microcapsules can be detected with real time US imaging (FIG. 5) so that their deposition at a precise and targeted location due to the vibrating delivery device visualized by the Ultrasound machine is made possible as well as an estimate of their lifetime in tumor (see FIG. 4B). Since US allows for real-time imaging of the tumor and ice ball contours it is possible at anytime to deposit the microcapsules at pre-selected sites, at iceball margins and in tumor, with extreme accuracy.

Also, there is the unique advantage of image assessment of local distribution of μcaps that allows re-dosing based on degradation/drug release rates; such re-dosing is timed to obtain maximum effect on tumor cells based on in vitro cytotoxicity assays using same drug microcapsules. Additional rounds of combined therapy are made possible with safety within tumor-tailored protocol(s).

While the above discussion is directed to a preferred embodiment, there are variations, which are effective in certain situations, for example:

1. Our invention describes the injection of thermosensitive microcapsules during a cryosurgical ablation session. They are deposited at the end of the freezing application and during the thaw period so that the drug diffuses immediately upon first intense release from the thermal stress, at infra-toxic doses. It has been found that 5Fu conc. in human colorectal tumor was 54 ng/g, 5 hours after oral administration of 5-DFUR-600 to 1200 mg/day orally for 3 to 5 days pre operatively- and about 33 ng/g after 6 to 9 hours, and 29 ng/g after 17 hours. The drug(s) acts upon tumor cells and vasculature in synergy with the cooling process that pre-sensitized them. A similar or better inhibitory effect is expected to happen with higher doses of the same microencapsulated drug acting in combination with partially or totally frozen cells.

2. Although our procedure makes use of the sequential combination of the cryotreatment first followed by the focal injection of μcaps chemotherapeutic, it is possible with same and/or different drug or drug combination, or tumor, to switch the order of the combination. For instance, another type of tumor may reveal more inhibition by being treated with local deposits of microencapsulated chemotherapy drugs followed by tumor cooling. Local deposition of free tumor inhibiting drugs can also be made just before the cryotherapy procedure, wherein the cytotoxic drug increases the efficacy of the cryoablation and the tumor inhibiting microcapsules retard and kill tumor cells that survive the freezing procedure. Since the thermosensitivity of our microcapsules can be adjusted at will, and given that the larger μcaps are more thermosensitive than the smaller one, it is another advantage of our invention to use the fast releasing μcaps during the selected triggering thermal stress (hypo and/or hyperthermia). Hence, a large dose of drug will be released for immediate and synergistic action on tumor cells during the thermal stress. The slow release type of μcaps deposited either during the perioperative or days after the operation will act on tumor cells for longer durations.

3. A combination of microencapsulated drugs can have a better effect on tumor growth inhibition. Numerous approved cytotoxic drugs and other agents that regulate tumor cell metabolism can be used for the treatment of solid malignant tumors. Other drugs that act as photosensitizer (like Photofrin®) are also of much interest. It is of particular interest to be able encapsulate or co-encapsulate different drugs that will allow for the combination of multiple treatment modalities on the same tumor. For instances a treatment scenario would combine the cryo-application with the injection of μcaps 5-FU a cytotoxic agent that is also a radio sensitizer. Tumor irradiation (brachytherapy, external beam therapy) would be a complementary treatment for any remnant lesion and to sterilize the peripheral margin of the lesion, after completion of the cryo-chemo treatment.

4. Such procedure opens the way to various modalities of combined focal cryo and chemo-ablative treatments. For instances instead of using a single cryoprobe to induce the target cooling, a multiprobe technique will do as well as any other modality of cryoablation known from those skilled in the art. The cryoablation process of hollowed organs tumor will use methods and devices already known in the field. For instances, a gas/liquid coolant spray of carbon dioxide ($CO_2$) would allow for treating extensive malignant lesions in surface (gastric, rectal, bladder carcinomas) or even pre-cancerous lesions. Vascular-mediated cooling of a tumor can also be used for the same purpose of triggering a chemo-sensitizing stress to tumor cells.

5. Although the duration of cold exposure of our thermosensitive microcapsules has been determined to a specific time of exposure in the context of a cryosurgical operation, it is possible that a shorter or longer time of exposure at similar or even higher temperature would give similar or better results. By adjusting the time temperature profile of exposure, we could manipulate the release rate of the drug to an optimal dose for the lesion at hand.

6. Although we have used this modality so far with a single cryoprobe and a single F/T cycle, a similar or better effect on tumor growth inhibition may be expected to result from the use of multiple cryoprobes used in conjunction and/or with multiple cryo (freeze) cycles to cover large tumor volumes and non-uniform tumor shapes.

7. Although our procedure makes use of a heat stress based on energy deprivation, energy deposition and lesion heating with RF, HIFU, ILT, MW, can be used alone or in conjunction with cryosurgery; immediately before or after the microcapsules interstitial injection(s). Such treatment would result in an equivalent or even better effect on the lesion, through a thermally modulated release of the microcapsule content that would be adjusted to the nature of the lesion and the purpose of the operation.

8. Although the preferred method of use of the invention uses cryotherapy, the same protocol is applicable to alternative ablative chemical, thermal, electrical or radiation methods that have the capability of triggering necrosis and apoptosis, or to increase cell permeability to drug. The combination of heat deposition techniques like, radiofrequency, hyperthermia (RF, HIFU, MW, laser), or ionizing radiation (brachytherapy, external beam), or chemicals like absolute alcohol, acetic acid, with microencapsulated imageable chemotherapy is applicable. The antitumor effects of HIFU a well-known non-invasive method for inducing tissue hyperthermia would be dramatically improved by the concurrent use of our local echogenic microcapsules chemotherapy. The microcapsules would locate specific tissue structures for treatment, allow for determining the focal point of the HIFU therapy transducer, thereby reducing the level of energy administered and usually required when a contrast agent is not used, and protect non-target tissue from damage by blocking the HIFU energy.

9. Although a preferred embodiment of the invention uses cryotherapy combined with microencapsulated 5-fluorouracil (μcaps 5-FU), the same concept is applicable to alternative carriers' embodiments, i.e. microcapsules containing one or more multiple drugs in combination. Those drugs are designed to inhibit tumor cell growth, metabolic functions, angiogenesis, including gene therapy, immune stimulants, or any other agent(s) known by those skilled in the art as being harmful to tumor cells.

10. Although a preferred embodiment describes the use of deposition of the imageable carriers directly into tumor, i.e. interstitially, the delivery, by continuous real-time visualization of catheters, having a resonant vibrating frequency, can be also accomplished within the vascular bed feeding the tumor by selective vascular catheterization as needed. A combination of vascular injection and interstitial deposition is also possible for a better distribution of the carriers within the tumor when it deems necessary. Given that the microcapsule size make them thrombogenic, the sustained release of the drug happens in a tumor that, after embolization, is rendered much more sensitive to chemotherapy and the drug(s) is now trapped into tumor. However, when it deems necessary, the embolization can be done with conventional methods, like glue, sponge fragments.

11. Although a preferred embodiment describes the percutaneous approach, the microcapsules can be delivered everywhere in the body where existing delivery devices can reach. Therefore, needle(s), catheter(s) can be used for delivering the drug-carriers to the right-targeted location(s) in tumor tissue as far as they can be set to vibrate at their resonant frequency. Since our vibrating system allows for adjusting optimal US visualization vibration to any sort of delivery device it's easy to get the drug-carriers inside tumors whether directly at open surgery, or through an endoscopic, percutaneous, or endoluminal approach with the help of the adapted catheters, needles.

12. Although a preferred embodiment describes the use of thermosensitivity as a means of drug(s) release from the microcapsules, mechanical, sonic, and/or chemical stresses can affect the microcapsule wall integrity. Specifically, microcapsules can be designed to break down when exposed to adjusted stresses with minimal collateral damages. For instances it's possible to expose the deposited carriers to low intensity US instead of HIFU, using a transducer, a much cheaper and less sophisticated treatment method that doesn't involve the formation of destructive or possibly mutagenic free radicals.

13. Although a preferred embodiment makes use of a single session of combined tumor cooling and interstitial deposition of imageable carriers, with subsequent injections of carriers alone into target tissues, multiple sequential and timely combined treatments can be as or more efficient at curing the remnant tumor cells. The subsequent sequences of treatment can use other types of thermal, mechanical or chemical stresses in combination with carriers deposition.

14. Although a preferred embodiment uses a thermal stress to sensitize cells to microencapsulated chemotherapy, an electrical stress known as electrosensitization obtained from short and intense electric pulses, can be used. A number of devices designed to facilitate delivery of electric pulses in vivo exist, Transdermal, laparoscopic, and catheter-mediated delivery systems (e.g. see International patent Applications WO 99/22809 A1, WO 99/06101 A1; WO 99/01157 A1, WO 99/01158) and allow access to any target in the human body.

15. Although a preferred embodiment may use an external US beam to trigger an immediate drug release from carriers' lysis, interstitial US transducer (s) can be used for the purpose of controlled release of the drug-carriers' load. The imageable delivery device, needle or catheter, can be used for this purpose that, upon activation after drug-carriers deposition, would trigger instant lysis of the carriers in close distance to the activated vibrating delivery tip. The frequency range of the vibration is adapted to allow for such lysis, from low to high frequency. The delivery device will be modified for this purpose and one or multiple US drivers could be used for imaging and for activating carriers' lysis.

Figure 3:
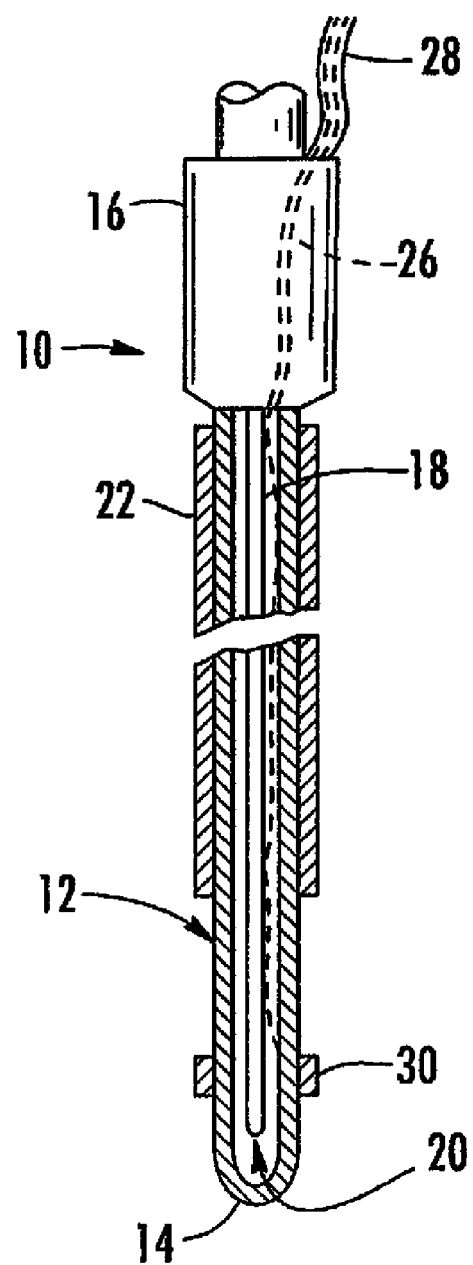
FIG. 3 a cross sectional view of a cryoprobe having a prezo crystal.

FIG. 3 illustrates an embodiment of the cryoprobe with integral sensing electrode, described in U.S. Pat. No. 6,235,018 and incorporated herein by reference. The probe includes a stainless steel shaft 12 that is rounded at its distal end 14 and has a handle 16 at its proximal end. An inner tube 18 delivers cryogenic fluid to the distal end 14 where it exits through an opening 20 and vaporizes to cool the metallic shaft 12. An insulating sleeve 22 surrounds the shaft and extends from the handle to a location near the tip 14. The center lead 26 in a coaxial cable 28 connects to the proximal end of the shaft. The prezo crystal 30 allows ultrasound or MR1 to pick up waves to locate the tip 14 while in a patient.

Although this invention has been shown and described with respect to detailed embodiments thereof, it will be appreciated and understood by those skilled in the art that various changes in form and detail thereof may be made without departing from the spirit and scope of the claimed invention.

We claim:

1. A medical procedure for treatment of tumors comprising the steps of reducing the temperature of a tumor by cryosurgery; delivering microcapsules containing a combination of a material capable of producing a viewable image and a cytotoxic drug, a tumor inhibiting drug, a photosensitizing drug, or combinations thereof, to the tumor; providing continuous real-time imaging of said microcapsules to facilitate precision placement of said microcapsules in the tumor at selected sites; and vibrating said microcapsules using an ultrasound device.

2. A medical procedure of claim 1 wherein said cryosurgery and said delivering of said microcapsules is performed simultaneously.

3. A medical procedure of claim 1 wherein said cryosurgery and said delivering of said microcapsules is performed sequentially.

4. A medical procedure of claim 1, wherein said microcapsules contain multiple drug payloads used for combinations of cytotoxic drugs, cytotoxic drugs followed by immunomodulators, or other combination drug strategies designed to inhibit target cell growth or critical metabolic functions.

5. A medical procedure of claim 1 wherein said microcapsules contain multiple drug payloads including cytotoxic drugs and anti-angiogenesis factors or gene therapy agents designed to reduce long term survival of the tumor.

6. A medical kit for treating a tumor, said kit comprising a cryosurgical apparatus for reducing the temperature of a tumor including at least one cryosurgical needle adapted for placement proximate to the tumor; a plurality of microcapsules containing a combination of cytotoxic drugs and a contrast material capable of producing a viewable image; a continuous real-time imaging resonant frequency apparatus adapted to produce said viewable image whereby placement of said microcapsules can be precisely delivered and controlled, said imaging apparatus adapted to facilitate the microcapsules release rate by vibrating said needle in contact with tumor tissue.

7. A medical kit for treating a solid tumor of claim 6 wherein said imaging apparatus acts as an active ultrasonic transducer, said ultrasonic imaging apparatus activating said microcapsules by vibration, said activation obtained by modulation of different frequencies of said ultrasonic transducer.

8. A medical kit for treating a solid tumor of claim 7 wherein said imaging apparatus includes more than one transducer, one of said transducers adapted to image said microcapsules and another adapted to activate said microcapsules.

9. A medical kit for treating a solid tumor of claim 6 wherein said needle or catheter has a tip, said tip adapted to be in direct contact with the tumor.

10. A medical kit for treating a solid tumor of claim 6 wherein a syringe is adapted to be connected to said needle, said syringe providing precise control over the delivery volume and distribution of said microcapsules.

* * * * *